United States Patent [19]

Singer et al.

[11] 4,147,800

[45] Apr. 3, 1979

[54] PEDICULICIDAL TOXICANTS

[75] Inventors: Arnold J. Singer, South Orange;
Myron J. Lover, Mountainside;
William E. Rhodes, III, Roselle;
William N. Bilodeau, Parsippany;
Donald M. Lynch, Union, all of N.J.

[73] Assignee: Block Drug Company, Inc., Kenilworth, N.J.

[21] Appl. No.: 759,638

[22] Filed: Jan. 17, 1977

[51] Int. Cl.² .................. A01N 9/02; A61K 31/23; A61K 31/045; A61K 31/22
[52] U.S. Cl. ............................ 424/312; 424/311; 424/343
[58] Field of Search ............... 424/312, 343, 311

[56] References Cited

U.S. PATENT DOCUMENTS 1,875,466  9/1932  Knight .................. 424/312
2,396,054  3/1946  McKim .................. 424/192

OTHER PUBLICATIONS

A Catalogue of Insecticides & Fungicides, Frear 1947, pp. 5 & 88–96.
Merck Index-9th Ed., 1976, p. 5069.
Chemical Abstracts 73:112852t (1970).

Primary Examiner—Leonard Shenkman
Attorney, Agent, or Firm—Ostrolenk, Faber, Gerb & Soffen

[57] ABSTRACT

An admixture of an aliphatic or aryl aliphatic alcohol and an aliphatic ester has been found pediculicidal.

17 Claims, 1 Drawing Figure

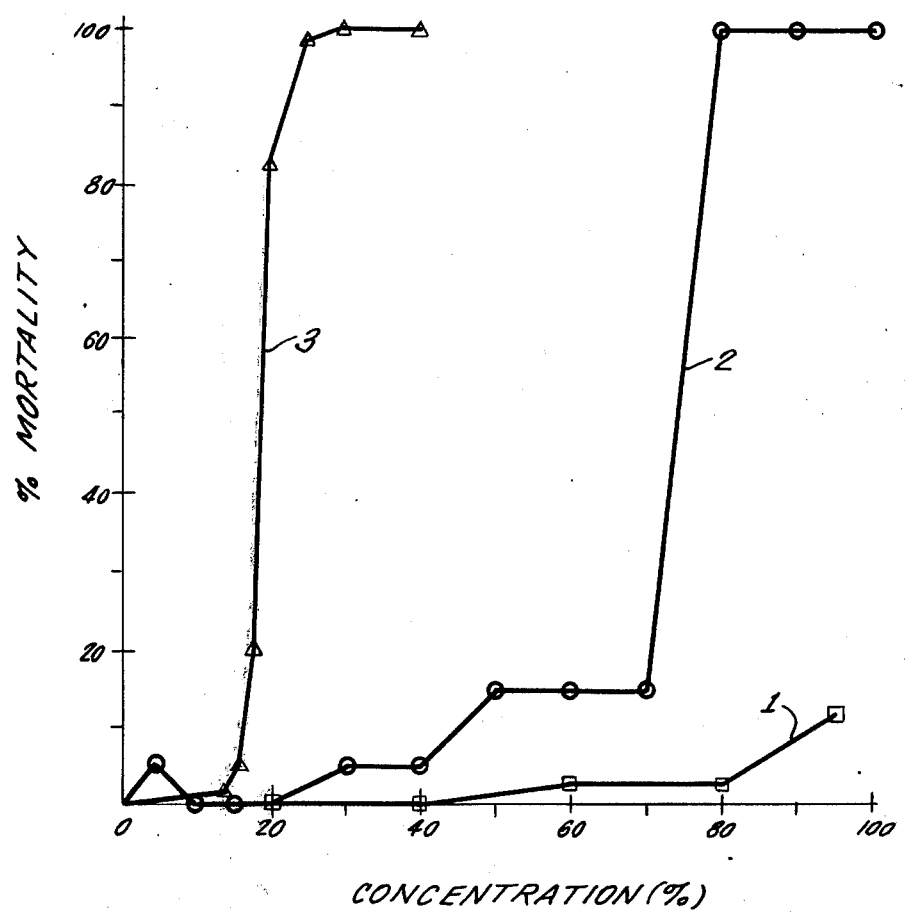

PEDICULICIDAL TOXICANTS

BACKGROUND OF THE INVENTION

There are only a relatively few pediculicides which are commercially available today. The most popular pediculicidal toxicants are Lindane (gamma benzene hexachloride), Malathion (S-1,2-dicarbethoxyethyl)-0,0-dimethyl phosphorodithioate), synergized pyrethrins and Cuprex (a combination of tetrahydronaphthalene, copper oleate and acetone, the acetone not asserted to be active).

Because of increased concern about the overall safety of some of the known ectoparasitic toxicants, the search for new, safe and effective pediculicides has intensified recently. It has now been discovered that the combination of an aliphatic alcohol and an aliphatic ester is synergistic as a pediculicide.

The results achieved in the instant invention are particularly surprising in view of the prior art. For example, one of the preferred ingredients, isopropanol has been used in Great Britain as a solvent for the Lindane and Malathion toxicants for some time. Additionally, investigations of the effect of various solvent system combinations for increasing the penetration of primary toxicants have been made. Wigglesworth, in "Permeability of Insect Cuticle," Nature, 147, 116 (January 1941), and "Some Notes on the Integument of Insects in Relation to the Entry of Contact Insecticides," Bull. Ent. Res., 33 205, (1942) describes the effect of oils and mixtures of oil and alcohol on insects including the louse. Hurst, in "Insect Cuticle as an Asymmetrical Membrane," Nature 147, 338 (March 1941), "Permeability of Insect Cuticle," Nature, 145, 462 (March 1940) and "Principals of Insecticidal Action as a Guide to Drug Reactivity—Phase Distribution Relationships," Trans. Faraday Soc. 39, 390 (1943), describes a mixture of kerosene and ethyl alcohol. However, Wigglesworth, Hurst, and others failed to perceive that such solvent systems, appropriately modified, could be used as pediculicides without the addition of a "primary toxicant." For example, McKim described the combination of a toxicant with a mixture of lower aliphatic alcohol and a hydrocarbon oil in U.S. Pat. No. 2,396,054 (1946). Moreover, both Wigglesworth and Hurst believed desiccation and imbibition were the means by which the polar/apolar combinations caused distress to insects. The findings that the instant pediculicides exhibit high activity in the presence of high percentages of water is therefore particularly surprising.

It is the object of this invention to provide new, safe and effective pediculicides and also to provide a safe and effective treatment for the control of ectoparasites such as lice. This and other objects of the invention will become apparent to those skilled in the art from the following detailed description.

SUMMARY OF THE INVENTION

This invention relates to ectoparasiticidal toxicants and a method of controlling ectoparasites. More particularly, the invention relates to a pediculicidal toxicant composition containing a mixture of an aliphatic or aryl aliphatic alcohol and an aliphatic ester. The invention also relates to the use of such compositions in controlling such ectoparasites.

DESCRIPTION OF THE PREFERRED EMBODIMENTS

The pediculicidal toxicant of the instant invention is an admixture of an aliphatic alcohol and an aliphatic ester. The combination is synergistic and retains its high level of activity when diluted in an inert pharmaceutically acceptable carrier, most notably an aqueous carrier.

The aliphatic alcohols employed in the instant invention are those somewhat water soluble aliphatic or aryl aliphatic alcohols containing 2 to about 8 carbon atoms and preferably 3 to 5 carbon atoms in the aliphatic moiety. Typical examples include ethyl alcohol, butyl alcohol, propyl alcohol, isopropyl alcohol, pentyl alcohol, tert-pentyl alcohol, hexyl alcohol, octyl alcohol and the like. The carbon atom chain can be either straight or branched and it is preferred that saturated alcohols be employed although unsaturated alcohols can also be used. In the toxicant composition, a single alcohol can be used or various mixtures of the alcohols can be employed. At present, the preferred alcohol is isopropanol. The water soluble aliphatic alcohols are, at best, feebly pediculicidal. In contrast, the aromatic alcohols such as benzyl alcohol, are pediculicidal alone, but are not as effective as aliphatic alcohols in aqueous combination with aliphatic esters. However, when the aryl moiety is separated from the hydroxyl moiety by a sufficient aliphatic chain, as in phenethyl alcohol, they behave like an aliphatic alcohol in this invention.

The esters employed in the present invention are aliphatic carbocyclic acid esters which contain 4 to about 32 carbon atoms. The preferred materials are esters of aliphatic alcohols of 1 to 8 carbon atoms, preferably 2 to 6 carbon atoms, and fatty acids of 12 to 24 carbon atoms, preferably 12 to 20 carbon atoms. Accordingly, the preferred esters generally contain 13 to 32 carbon atoms and most preferably 14 to 26 carbon atoms. Among the esters which can be employed are ethyl acetate, propyl acetate, methyl laurate, ethyl laurate, propyl laurate, isopropyl laurate, butyl laurate, isobutyl laurate, amyl laurate, isoamyl laurate, methyl stearate, ethyl stearate, propyl stearate, isoamyl stearate, isobutyl stearate, ethyl oleate, propyl oleate, isopropyl oleate, isobutyl oleate, methyl myristate, ethyl myristate, propyl myristate, isopropyl myristate, butyl myristate, isobutyl myristate, amyl myristate, isoamyl myristate, myristyl myristate, and the like. The presently preferred ester is isopropyl myristate. In the pediculicidal toxicants of the instant invention, the ester can be a single compound or a mixture of two or more compounds.

The aliphatic esters exhibit good pediculicidal properties when applied in a substantially pure form, i.e., in a concentration of at least 70% or more. Obviously, application of the esters in such a form is somewhat inconvenient and inappropriate. In the present invention, the ester is employed in an amount which is usually less than one half of the total toxicant composition employed. With respect to the total weight of the aliphatic alcohol and aliphatic ester, the weight ratio of the former to the latter is usually about 1.1:1 to 3:1 and preferably about 1.3:1 to 1.7:1.

The active pediculicidal toxicant mixture of this invention, the aliphatic alcohol and aliphatic ester, can be used in the form of liquids, powders, lotions, creams, gels or aerosol sprays or foams by formulation with inert pharmaceutically acceptable carriers by procedures well known in the art. Any pharmaceutically acceptable carrier, whether aqueous or non-aqueous, which is inert to the active ingredient mixture can be employed. By inert is meant that the carrier does not have a substantial detrimental effect on the pediculicidal toxicant activity of the alcohol-ester admixture. A significant and surprising advantage of the instant composition is that an aqueous carrier can be employed. The presence of significant amounts of water has obvious economic advantages but, more importantly, water greatly reduces the skin and eye irritation liability to the patient. The Draize test is a recognized procedure for assessment of eye irritation and isopropanol, the preferred alcohol of this invention, has been used for calibration of the test because it causes a high degree of eye damage. The instant compositions, for example containing 25% isopropanol with water and other components, have shown zero Draize irritation.

The alcohol-ester admixture is incorporated into the composition used to treat the substrate in need of such treatment, believed to be in need of such treatment, or desired to be prophylactically protected in an effective pediculicidal toxic amount. By such amount is meant the amount which will cause virtually 100% of the lice exposed in the two or four minute immersion test described below to die within 24 hours. It has been found that an effective pediculicidal toxic amount can be obtained when the amount of the aliphatic alcohol in the treating composition is at least about 20 percent by weight and the amount of the aliphatic ester is at least about 15 percent by weight. Obviously, amounts of the alcohol and ester in excess of these minimum amounts can be employed but there appears to be no significant advantage if the percentages are significantly in excess of those stated. It will also be apparent from the foregoing that a liquid carrier can constitute up to about 65 weight percent of the treating composition. Preferably the carrier constitutes about 40–60%.

The two or four minute immersion test referred to in the preceding paragraph is carried out as follows. A 50 ml beaker is filled with tap water and allowed to come to room temperature (about 24° C.). Ten young adult male and ten young adult female lice (*Pediculus humanus corporis*) of the same age group and from the same stock colony are placed on a 2 × 2 cm coarse mesh patch. The sample to be tested, maintained at room temperature, is shaken until homogenous and placed into a 50 ml beaker. The mesh patch is placed into the sample immediately after pouring, allowed to submerge, and after either two or four minutes is removed and immediately plunged into the beaker containing the tap water. The patch is vigorously agitated every ten seconds and after one minute the patch is removed and placed on paper toweling. The lice are then transferred to a 4 × 4 cm black corduroy cloth patch and this point of time is considered 0 hours. Thereafter, the corduroy patch is placed in a petri dish which is covered and stored in a 30° C. holding chamber.

The synergistic effect of the alcohol-ester combination can be appreciated from the following results of the four minute immersion test. Six samples were prepared by mixing isopropanol and/or isopropyl myristate with 7 parts by weight of Polysorbate 80, an inert emulsifier, and water q.s. ad. 100%. The results achieved were:

|  | % Dead |
|---|---|
| 42w % of 95% isopropanol | 7.5 |
| 15w % of isopropyl myristate in inert vehicle | 5 |
| 42w % of 95% isopropanol, and 15w % of isopropyl myristate in inert vehicle | 100 |
| 20w % of 95% isopropanol and 15w % of isopropyl myristate in inert vehicle | 75 |
| 42w % of 95% isopropanol and 10w % of isopropyl myristate in inert vehicle | 60 |
| 25w % of isopropanol and 15w % of isopropyl myristate in inert vehicle | 100 |

The synergistic effect of the present invention can also be appreciated from the sole FIGURE which is a graph of lice mortality versus concentration in the two minute immersion test described above. Several test compositions were used each containing 7 weight percent of Polysorbate 80 (an inert surfactant) and water q.s. ad. 100%. Curve 2 represents the test composition containing varying concentrations of isopropyl myristate and curve 1 represents the test compositions containing varying concentrations of isopropyl alcohol. It will be noted that the compositions containing only the isopropyl alcohol up to 95% never achieved a percent mortality in excess of 15% (at 100% concentration, mortality was 65%) and it required not less than 70% of the isopropyl myristate to achieve a 100% mortality. Curve 3 represents the results achieved with test compositions containing 15% isopropyl myristate and varying percentages of isopropyl alcohol. 100% mortality was achieved in this two minute test when the isopropyl alcohol concentration reached 30 weight percent.

Other examples of alcohol-ester combinations which can be used within the context of the instant invention include butanol and ethyl stearate, pentanol and methyl laurate, octanol and isobutyl oleate, ethanol and myristyl myristate, ethanol and butanol and isopropyl myristate, isopropyl alcohol and ethyl stearate and isopropyl myristate, ethanol and butanol and ethyl stearate and isobutyl oleate and the like.

Various alcohol-ester combinations were evaluated in the two minute immersion test described above. The results are set forth in the following tables. It will be appreciated that the mortality results set forth represent only the particular material tested and should not be interpreted to mean that other concentrations, are not pediculicidal.

In Table I, the results of the testing using aliphatic monoesters undiluted or in a combination containing 25% isopropanol (IPA) and 60% aqueous carrier are set forth.

TABLE I

| Esters | 100% Ester | 15% Ester, 25% IPA, 60% aqueous carrier |
|---|---|---|
| Ethyl Acetate | 100 | 95 |
| Ethyl Cyanoacetate | 0 | 5 |
| Butyl Acetate | 100 | 95 |
| Ethyl Acetoacetate | 0 | 5 |
| Ethyl 4-Chlorobutyrate | 80 | 5 |
| Butyl Lactate | 25 | 85 |
| Ethyl Levulinate | 5 | 0 |
| Ethyl Caproate | 100 | 100 |
| Ethyl Caprylate | 100 | 100 |
| Methyl Caprate | 100 | 100 |
| Ethyl Caprate | 100 | 100 |

TABLE I-continued

| Esters | 100% Ester | 15% Ester, 25% IPA, 60% aqueous carrier |
|---|---|---|
| Methyl Laurate | 100 | 100 |
| Ethyl Laurate | 100 | 100 |
| Methyl Myristate | 95 | 100 |
| Isopropyl Laurate | 100 | 100 |
| Lauryl Lactate | 100 | 100 |
| Isopropyl Myristate | 100 | 100 |
| Methyl Palmitate | * | 90 |
| Butyl Myristate | 100 | 100 |
| Isononyl Isononanoate | 100 | 100 |
| Isopropyl Palmitate | 95 | 100 |
| Cetyl Lactate | * | 100 |
| Isopropyl Linoleate | 85 | 35 |
| Isopropyl Isosterate | 100 | 100 |
| Butyl Stearate | 80 | 95 |
| 2-Ethylhexyl Palmitate | 100 | 100 |
| Decyl Oleate | 70 | 100 |
| Myristyl Myristate | ** | 100 |

*solid - could not be tested at 100%
**solidified upon contact with rinse.

The foregoing results show that the aliphatic monoesters containing 4 to 28 carbon atoms are potent pediculicides and when combined with 25 weight percent isopropanol and 60% aqueous carrier are highly pediculicidal. The presence of various functional groups such as the 2-nitrile, 3-or 4-keto, 2-hydroxy, 4-chloro and unsaturation in the acid moiety of the ester reduces pediculicidal activity. Reduction in activity, however, can be offset by extension of the chain length as shown by the activity of the combinations of lauryl lactate, cetyl lactate, and decyl oleate.

In Table II, various aliphatic alcohols were evaluated alone, in aqueous solution, and in solution with 15 weight percent of isopropyl myristate (IPM) and 60% aqueous carrier.

TABLE II

| Alcohol | 100% Alcohol | 15% IPM, 25% Alcohol, 60% aqueous carrier | 25% Alcohol 75% aqueous carrier |
|---|---|---|---|
| Methanol | 0 | 0 | 0 |
| Ethanol | 45 | 0 | 0 |
| iso-Propanol | 65 | 100 | 0 |
| n-Propanol | 70 | 100 | 0 |
| iso-Butanol | 95 | 100 | 40 |
| sec-Butanol | 95 | 100 | 0 |
| t-Butanol | 80 | 100 | 0 |
| n-Butanol | 100 | 100 | 20 |
| iso-Pentanol | 100 | 100 | 55 |
| n-Pentanol | 100 | 100 | 10 |
| n-Hexanol | 100 | 100 | 5 |
| n-Octanol | 100 | 40 | 10 |
| n-Decanol | 100 | 60 | 20 |
| n-Dodecanol | 100 | 45 | 10 |
| Hexadecanol | 100 | 35 | 40 |
| Oleyl Alcohol | 100 | 0 | 0 |

In Table III, 5 aliphatic diesters are set forth.

TABLE III

| Diester | 100% Ester | 15% Ester, 25% IPA, 60% aqueous carrier |
|---|---|---|
| Diethyl Oxalate | 20 | 5 |
| Diisopropyl Adipate | 100 | 40 |
| Dimethyl Sebicate | 100 | 5 |
| Dimethyl Brassylate | 100 | 95 |
| Di-n-hexyl Azelate | 85 | 20 |

In Table IV, the results achieved using aryl mono and diesters are set forth.

TABLE IV

| Aryl Ester | 100% Ester | 15% Ester, 25% IPA 60% aqueous carrier |
|---|---|---|
| Benzyl Benzoate | 95 | 5 |
| Diethyl Phthalate | 0 | 5 |
| Dibutyl Phthalate | 60 | 10 |
| Dioctyl Phthalate | 40 | 10 |

The mortalities achieved using 2 aryl alkyl alcohols are set forth in Table V.

TABLE V

| Alcohol | 100% Alcohol | 15% IPM, 25% Alcohol 60% aqueous carrier |
|---|---|---|
| Benzyl alcohol | 90 | 75 |
| Phenethyl alcohol | 100 | 100 |

As noted above, the pediculicidal compositions of this invention can be formulated into a variety of end use forms. Typical formulations are set forth below in which IPA represents isopropyl alcohol, IPM represents isopropyl myristate, and the amounts set forth are percentages by weight.

Clear liquid pediculicide, suitable for mechanical spray application or inunction

| | |
|---|---|
| IPA | 65 |
| IPM | 10 |
| Water | 25 |

Pediculicidal Shampoo, clear liquid

| | |
|---|---|
| IPA | 25 |
| IPM | 15 |
| Triethanolamine lauryl sulfate | 20 |
| Water | 40 |

Pediculicidal Aerosol Fast Breaking Foam

| | |
|---|---|
| IPA | 25 |
| IPM | 15 |
| Mono and Diglycerides of Edible Fats or Oils | 5 |
| Water | 42 |
| Glycerine | 3 |
| Isobutane | 10 |

Pediculicidal Aerosol Spray

| | |
|---|---|
| IPA | 65 |
| IPM | 10 |
| Isobutane | 10 |
| Water | 15 |

Pediculicidal Aerosol Spray

| | |
|---|---|
| IPA | 25 |
| IPM | 15 |
| Isobutane | 15 |
| Water | 40 |
| Polysorbate 80 | 5 |

Pediculicidal Gel

| | |
|---|---|
| IPA | 25.0 |
| IPM | 15.0 |
| Carbopol 940 | 0.5 |

-continued

| | |
|---|---|
| Triethanolamine | 0.38 |
| Water | 59.22 |

Pediculicidal Powder*

| | |
|---|---|
| Pyrophyllite | 90.0 |
| IPA | 6.5 |
| IPM | 3.5 |

*In a dry inert carrier formulation, the carrier can range up to about 95%.

Pediculicidal Lotion

| | |
|---|---|
| Triethanolamine Stearate | 20 |
| Cetyl Alcohol | 5 |
| IPA | 25 |
| IPM | 15 |
| Water | 35 |

Pediculicidal Stick

| | |
|---|---|
| Sodium Stearate | 60 |
| IPA | 25 |
| IPM | 15 |

Pediculicidal Lotion

| | |
|---|---|
| Ethanol | 50.0 |
| Sodium carboxymethylcellulose | 0.2 |
| Carbopol 941 | 0.2 |
| IPM | 15.0 |
| Triethanolamine | 0.2 |
| Acetylated polyoxyethylated (10) lanolin | 3.0 |
| Water | 31.4 |

Pediculicidal Lotion

| | |
|---|---|
| Polyoxyethylene (10) cetyl ether | 3.0 |
| Talc | 1.5 |
| Carbopol 941 | 0.3 |
| Triethanolamine | 0.3 |
| Ethyl alcohol | 40.0 |
| IPM | 15.0 |
| Water | 39.9 |

Various changes and modifications can be made in the instant invention without departing from the spirit and scope thereof. The various embodiments disclosed herein were for the purpose of further illustrating the invention but were not intended as limiting. Throughout this specification and claims, all temperatures are in degrees centigrade and all parts and percentages are by weight unless otherwise indicated.

What is claimed is:

1. A method of controlling lice which comprises applying to a host in need of such control a pediculicidal toxic amount of a mixture of (1) at least one aliphatic alcohol of 2 to about 8 carbon atoms and (2) at least one aliphatic carboxylic acid ester of 4 to about 32 carbon atoms, wherein the ratio of said alcohol to said ester is present in a synergistically effective amount of about 1.1:1 to 3:1.

2. The method of claim 1 wherein said alcohol is an aliphatic alcohol of 3 to 5 carbon atoms and said ester contains 13 to 32 carbon atoms.

3. The method of claim 2 wherein said ester contains 14 to 26 carbon atoms.

4. The method of claim 1 wherein said ratio is about 1.3:1 to 1.7:1.

5. The method of claim 1 wherein said mixture is employed in combination with an inert pharmaceutically acceptable carrier and wherein said alcohol is an aliphatic alcohol present in an amount of at least about 20 weight percent and said ester is at least about 15 weight percent of the combined weight of said mixture and carrier.

6. The method of claim 5 wherein said carrier constitutes about 40 to 60 weight percent of the combined weight of said mixture and said carrier.

7. The method of claim 5 wherein said carrier is an aqueous carrier.

8. The method of claim 7 wherein said carrier is about 40 to 60 weight percent based on the total weight of said mixture and said carrier.

9. The method of claim 8 wherein said alcohol is isopropanol and said ester is isopropyl myristate.

10. The method of claim 1 wherein said mixture is contacted with said lice.

11. A pediculicidal toxicant composition consisting essentially of an aqueous mixture of an aliphatic alcohol of 3 to 5 carbon atoms and an aliphatic carboxylic acid ester of 4 to about 32 carbon atoms, the weight ratio of said alcohol to said ester being present in a synergistically effective amount of about 1.1:1 to 3:1.

12. The toxicant of claim 11 wherein said alcohol is an aliphatic alcohol, said carboxylic acid ester has 13 to 32 carbon atoms and wherein said ratio is about 1.3:1 to 1.7:1.

13. A pediculicidal toxicant comprising at least 20 weight percent of an aliphatic alcohol of 3 to about 5 carbon atoms, at least about 15 weight percent of an aliphatic carboxylic acid ester of 4 to about 32 carbon atoms and an inert aqueous pharmaceutically acceptable carrier, wherein the ratio of alcohol to ester is present in a synergistically effective amount of about 1.1:1 to 3:1.

14. The toxicant of claim 13 wherein said alcohol is an aliphatic alcohol, said ester has 13 to 32 carbon atoms, said aqueous carrier is about 40 to 60% of said toxicant.

15. The toxicant of claim 13 wherein said ester has 14 to 26 carbon atoms and wherein said ratio is about 1.3:1 to 1.7:1.

16. The toxicant of claim 14 wherein said alcohol is isopropanol, said ester is isopropyl myristate and wherein said aqueous carrier is water.

17. A pediculicidal toxicant composition consisting essentially of a mixture of isopropanol and isopropyl myristate in a synergistically effective ratio of about 1.1:1 to 3:1, respectively.

* * * * *